(12) United States Patent
Dunham

(10) Patent No.: US 8,597,672 B2
(45) Date of Patent: Dec. 3, 2013

(54) OWL EFFIGY

(76) Inventor: Fred Dunham, Spokane, WA (US)

( * ) Notice: Subject to any disclaimer, the term of this patent is extended or adjusted under 35 U.S.C. 154(b) by 0 days.

(21) Appl. No.: 13/590,285

(22) Filed: Aug. 21, 2012

(65) Prior Publication Data

US 2012/0312249 A1 Dec. 13, 2012

Related U.S. Application Data

(62) Division of application No. 11/868,863, filed on Oct. 8, 2007.

(51) Int. Cl.
A61K 31/24 (2006.01)
A01M 29/06 (2011.01)
A01N 25/34 (2006.01)

(52) U.S. Cl.
USPC .......................................... 424/405; 119/712

(58) Field of Classification Search
USPC ........................................................ 424/405
See application file for complete search history.

(56) References Cited

U.S. PATENT DOCUMENTS

| 5,379,545 | A | * | 1/1995 | Gall et al. | 43/131 |
|---|---|---|---|---|---|
| 5,527,531 | A | * | 6/1996 | Linhart | 424/410 |
| 6,328,986 | B1 | * | 12/2001 | Ballinger, Jr. | 424/405 |
| 6,517,009 | B2 | * | 2/2003 | Yahav | 239/70 |
| 6,958,146 | B2 | * | 10/2005 | Askham et al. | 424/84 |
| 7,867,479 | B2 | * | 1/2011 | Dunham et al. | 424/84 |
| 8,092,790 | B2 | * | 1/2012 | Dunham et al. | 424/84 |
| 2003/0194454 | A1 | * | 10/2003 | Bessette et al. | 424/745 |
| 2005/0160654 | A1 | * | 7/2005 | Cosciani | 43/2 |

OTHER PUBLICATIONS

Stevens et al. "The Use of Aerosol Repellents as an Avian Deterrent Strategy", 1998, previously cited in parent U.S. Appl. No. 11/868,863.*

* cited by examiner

Primary Examiner — Richard Schnizer
Assistant Examiner — Audrea Buckley
(74) Attorney, Agent, or Firm — Brian J. Pangrle

(57) ABSTRACT

An assembly can include a hollow owl effigy with holes, methyl anthranilate and a carrier to carry the methyl anthranilate within the hollow owl effigy and to retard release of the methyl anthranilate through the holes of the hollow owl effigy. Other devices, system and methods are also disclosed.

17 Claims, 9 Drawing Sheets

OWL EFFIGY

RELATED APPLICATION

This application is a divisional of co-pending U.S. patent application Ser. No. 11/868,863, filed 8 Oct. 2007, which is incorporated by reference herein.

TECHNICAL FIELD

The subject matter disclosed herein generally relates to effigies.

BACKGROUND

Birds destroy and contaminate valuable crops, leave unsightly messes on and beneath roosting areas, and damage and corrode equipment finishes and electrical connections in stored machinery in equipment sheds, barns, and other structures. In addition to being unpleasant and destructive, their droppings can also pose a health hazard.

A method of abating bird damage is the use of predator effigies such as owls, snakes, and scarecrows. The success of these effigies has been very limited as birds, after an initial fright response, can and do quickly determine that these effigies are not real predators. The effective life of these effigies is typically measured in days, if not hours.

Another method of abatement is the use of irritant bird repellents. These repellents are applied either by spraying, coating or fogging the crop, structure or area from which birds are to be excluded. While generally effective, these repellents can affect taste, and as a result cannot be used on such crops as wine grapes. In addition, no currently available approved repellent is organically certified, so they cannot be applied to organically grown crops. Thus, yields for such crops are often diminished, which results in higher prices. On or within structures, repellents can take a significant amount of time to exclude birds, and repellents typically dissipate before they can be effective, requiring time consuming and expensive re-treatment. Further, repellent residue can build up on valuable crops, structures or equipment, which may act to attract airborne debris. Overall, a need exists for improved devices and techniques for bird abatement.

BRIEF DESCRIPTION OF THE DRAWINGS

A more complete understanding of the various devices, methods, systems and/or arrangements described herein, and equivalents thereof, may be had by reference to the following detailed description when taken in conjunction with the accompanying drawings wherein.

DETAILED DESCRIPTION

The following description includes the best mode presently contemplated for practicing various described implementations. This description is not to be taken in a limiting sense, but rather is made merely for the purpose of describing the general principles of the various implementations. The scope of the described implementations should be ascertained with reference to the issued claims.

It was known from the late 19th century work of Nobel laureate Ivan Pavlov that an animal could be conditioned to react in a predictable manner through repeated association of a response to be learned with an innate reflexive response. As described herein, it was hypothesized that by infusing a predator effigy with a repellent, a bird's reflexive fright response to the visual cue of the predator effigy would be reinforced by the bird's inherent avoidance response to the irritant in the repellent, and visa versa, thus each reflexive response reinforcing the other in a positive feedback loop, thereby increasing the efficacy of both methods of abatement.

In addition, it was hypothesized that by filling or infusing the effigy with the repellent by way of a container or porous substrate, or mixing with an absorbent material, or amorphous material such as a wax or gel, less of the expensive repellent could be used, application would be simplified, and the effigy would provide protection of the repellent eliminating the problem of rapid dissipation, thus greatly increasing the life of the repelling effect and decreasing re-application costs.

Finally, because these effigies could be put in close proximity to taste sensitive or organically grown crops without actually being applied to the crop, they would provide much needed protection without destroying the taste or organic certification of the crop to be protected.

Evidence from various trials prove the aforementioned hypotheses. Accordingly, various exemplary systems, devices and methods are described below that pertain to bird abatement.

Figure 1:
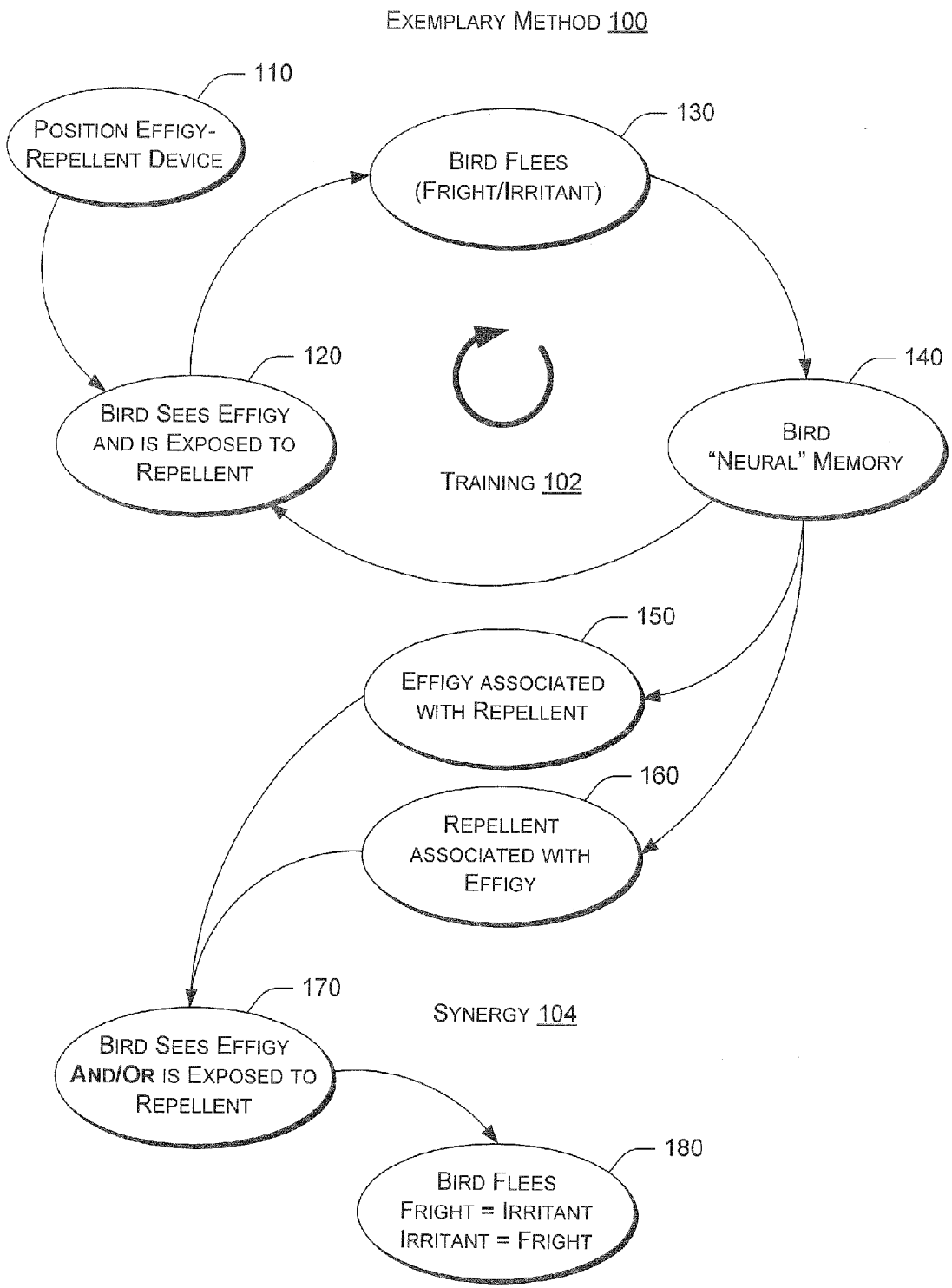
FIG. 1 is a block diagram of an exemplary method for modifying behavior of an animal.

FIG. 1 shows an exemplary method 100 that includes a training phase 102 and a synergy phase 104. The training phase 102 commences with positioning an effigy-repellent device 110. For example, the device may be positioned in a field of crops or in a storage shed for storing crops or equipment. Effigies of terrestrial animals may be positioned on the ground while effigies of arboreal animals may be elevated. In step 120, a bird sees the effigy and is exposed to the repellent. In turn, per step 130, the bird flees due to its fright response to the effigy and due to an irritant response to the repellent.

The method 100 enters a synergy phase 104 that develops according to the training phase step 140 where the bird's memory acts to associate the fright response to the effigy with the irritant response of the repellent 150 and/or to associate the irritant response of the repellent with the fright response to the effigy 160. In the synergy phase 104, per step 170, if the bird sees an effigy, it will associate this effigy with the irritating effect of the repellent and/or if the bird is exposed to a repellent (acting according to the same mechanism), then the bird will associate the irritation with the fright response of the effigy. Accordingly, per step 180, the bird flees as it associates fright with irritant and/or irritant with fright.

In the method 100, the fright response may be learned or genetic. For example, ducklings will run for shelter upon seeing the silhouette of a highflying hawk, likely a genetic response; whereas, a scarecrow (human effigy) is likely a learned response. The irritant response may be due to any of a variety of mechanisms. For example, methyl anthranilate is a potent, congenital trigeminal nerve irritant in birds (e.g., avian irritant). Irritation of the trigeminal nerve by methyl anthranilate causes a reflexive avoidance response in birds (see, e.g., Kirifides et al., "Calcium responses of chicken trigeminal ganglion neurons to methyl anthranilate and capsaicin", *The Journal of Experimental Biology* 207:715-722 (2004)). For humans, irritation of the trigeminal nerve and the condition known as trigeminal neuralgia can generate pain that is described as among the most acute known to mankind. Trigeminal nerualgia is described as produces excruciating, lightning strikes of facial pain, typically near the nose, lips, eyes or ears. For humans and many mammals, capsaicin (e.g., the active component in chili peppers) is a trigeminal nerve irritant while methyl anthranilate (e.g., as occurring in concord grapes) is not known as an irritant. For birds, the reverse is largely true, noting that high levels of capsaicin can irritate the avian trigeminal nerve.

While various examples described herein pertain to birds, techniques may be adapted to abatement of animals. For example, as mentioned, mammals have an aversion response to capsaicin. Thus, an effigy of a predator may be treated with or contain capsaicin where the capsaicin may diffuse into the surrounding environment or be driven by convection such that the effigy causes a fright response and the capsaicin causes an aversion response in a mammal.

As described herein, an exemplary method for modifying behavior of an animal includes simultaneously providing an effigy of a predator for the animal and a repellent that comprises a trigeminal nerve irritant for the animal where sight of the effigy causes a fright response and exposure to the repellent causes an aversion response, where the animal forms an association between the fright response and the aversion response and where the association reinforces the fright response of the animal to sight of the effigy. In such a manner, even if a reservoir for the repellent is depleted, the effigy alone will still be more effective than if the effigy and repellent combination had not been used to modify the behavior of the animal.

An exemplary technique described herein combines a predator effigy with a bird repellent. For example, an exemplary effigy may be a folded box with a picture and/or shape of an owl where the box at least partially surrounds a container of repellent. Such a technique can provide synergistic advantages over effigies alone and over repellents alone. For example, an effigy infused, filled with or otherwise containing a bird repellent can provide a synergistic effect, reinforcing the bird's initial fright response to the predator effigy with the repelling effect of the repellent, thus conditioning the bird to avoid areas where the effigy is placed. In such an example, a predator effigy can provide protection and a reservoir for repellent. In various examples, an effigy dissipates repellent at a rate that can act more effectively than periodic atmospheric spraying alone.

An exemplary effigy supplied with repellent optionally provides a substantially zero order concentration of repellent over a period of time when placed in a structure (e.g., a barn, a shed, etc.) until the supply of the repellent is depleted. In various examples, techniques to control or optimize release can economize repellent usage. Such techniques, when combined with effigy synergy, can provide economic and performance advantages when compared to repellent atmospheric spraying alone and effigy use alone.

Various exemplary methods are also discussed below. For example, a method for repelling birds includes using a visual representation of a prey animal (e.g., an effigy) and a repellent within representation of the prey animal. Various methods include techniques for dispersing repellent, signaling a user, controlling a circuit, etc.

FIG. 2 shows an exemplary arrangement of a compound 210 that affects bird behavior (e.g., promotes avian avoidance behavior) and an effigy 220 that may be selected from a group of predator effigies, including human effigies. In the example of FIG. 2, the compound is methyl anthranilate (MA), which is a bird repellent.

Birds demonstrate a congenital aversion to MA, a chemical compound found in the skin of grapes (*Vitus* spp.), at concentrations that do not evoke behavioral responses from mammals. The reflexive avoidance of MA in birds is mediated through the trigeminal pathway. There exists considerable information on the effects of such exogenous compounds on avian avoidance behavior.

Chemesthesis is the perception of chemically irritating or painful nociceptive stimuli. MA is an aversive chemical to birds and it is primarily detected by way of the trigeminal system rather than the olfactory. Some of the avoidance of MA and similar bird repellents might involve detection of olfactory cues but their irritant function is primarily or solely by way of the trigeminal pathway. Trigeminal irritants exert their influence when applied orally, nasally, or ocularly. Chemicals such as anthranilates and acetophenones (e.g., o-acetophenone) are repellent to birds and known to irritate via the trigeminal pathway. Coniferyl benroates are aromatic compounds with structural properties similar to the anthranilates and known irritants. An exemplary compound is a bird irritant that operates via at least the avian trigeminal pathway.

Some exemplary compounds include cyclic carbon-carbon bonds. Some exemplary compounds include aromatic carbon-carbon bonds. Most exemplary compounds include at least one oxygen atom bound to at least one carbon atom. Such compounds may exist as aldehydes, alcohols, carboxylic acids, ketones, esters, ethers and/or other types of compounds. Of course, depending on pH, etc., deprotonation or protonation may occur or a compound may exist as a salt. With respect to salts, any suitable counter ion may suffice, such as, but not limited to, sodium ions, potassium ions, ammonium ions, monoethanolamine ions, diethanolamine ions, triethanolamine ions, and/or other nitrogen containing ions.

Further, exemplary compounds that exist as ions may be paired with other ionic chemical species. For example, an exemplary compound that includes an amine may serve as a counter ion to an anionic chemical species and/or to neutralize an acid.

Some exemplary compounds include a six carbon aromatic ring (e.g., a benzene ring) having one or more moieties (e.g., group or chain) bound thereto. In general, such exemplary aromatic compounds include a moiety that includes at least one oxygen atom. For example, methyl anthranilate (formula weight of approximately 151 and also known as methyl 2-aminobenzoate, methyl 3-aminobenzoate, etc.) has an ester moiety and 4-pentenophenone (formula weight of approximately 160 and marketed as LAVONAX™, IFF, New Jersey) has a ketone moiety. Other exemplary compounds, such as, bisabolene (formula weight of approximately 204), include an unsaturated six carbon ring and do not include any oxygen atoms.

An exemplary composition includes a commercially available product marketed as BIRDSHIELD™ (Bird Shield Repellent Corp., Spokane, Wash.) having methyl anthranilate as an active ingredient. Information disclosed in U.S. Pat. No. 5,296,226, entitled "Bird Repellent Compositions", is incorporated by reference herein. The commercially available product marketed as BIRDSHIELD™ includes the exemplary compound methyl anthranilate, and includes fatty acids and/or surfactants. Use of such a product can reduce a need for adhering and/or spreading agents, for example, in an exemplary compositions and/or an exemplary method.

With respect to a predatory effigy 220, the group of possible predatory effigies includes birds, reptiles, and mammals including humans. In ecology, predation describes a biological interaction where a predator species kills and eats other organisms, known as prey. Often, predators or predator effigies alone act to repel birds (e.g., prey birds).

Figure 2:
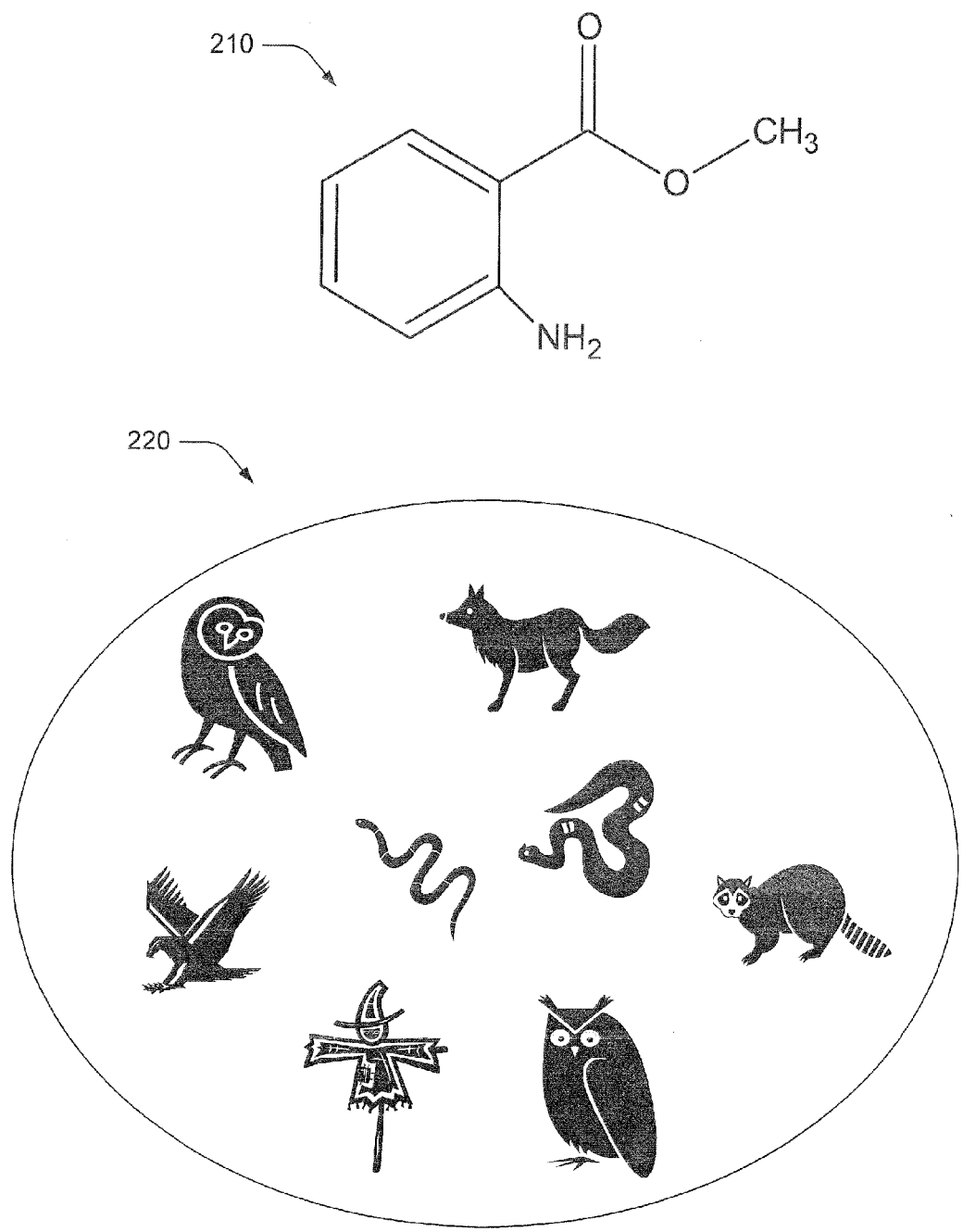
FIG. 2 is a diagram for an exemplary arrangement that includes a compound for affecting bird behavior and an effigy.

The group of FIG. 2 includes, for example, owls, hawks, falcons, foxes, opossums, weasels, raccoons, snakes and scarecrows. Birds of prey (raptors) are general birds with keen eyesight, strong curved beaks and long curved strong talons. Diurnal raptors (Falconiformes—hawks, falcons, eagles, kites, harriers) such as the red-tailed hawk hunt during the day and nocturnal raptors (Strigiformes—owls) such as the great horned owl hunt mostly at night. Vultures are also considered birds of prey.

There are over 200 species of Falconiformes and 150 species of Strigiformes. North American raptors range in size from the small American Kestrel to the very large Bald Eagle. There are raptors on every continent except Antarctica.

Owls and hawks are predators not only to rodents on our properties but also to the smaller birds such as sparrows or chickadees. Owls typically eat mostly mice, moles, shrews, rats, gophers, squirrels and only a small part of their food is birds some of which are grouse, quail, jays, cardinals, crows and small birds. A Table 1 below lists birds consumed by some owls.

TABLE 1

Owls and Consumption of Birds.

| | |
|---|---|
| Barn Owl | Pigeons, jays, Green Herons, sparrows, Grackles, starlings, meadowlarks, flickers, Bluebirds, swallows, towhees |
| Barred Owl | Doves, grouse, quail, flickers, crows, jays, Cardinals |
| Burrowing Owl | Sparrows, vireos, meadowlarks, Horned Larks |
| Great Horned Owl | Grebes, ducks, geese, bitterns, rails, coots, grouse, Mourning Doves, meadowlarks, juncos, sparrows, robins, mockingbirds, jays, flickers |
| Hawk Owl | Ruffed Grouse, sparrows |
| Long-eared Owl | Starlings, Blue Jays, Cardinals, towhees, juncos, Horned Larks, Red-winged Blackbirds, meadowlarks, Brown Thrashers, Bluebirds, American Goldfinches |
| Saw-whet Owl | Sparrows, juncos |
| Short-eared Owl | Meadowlarks, Savannah Sparrow, Sharp-tailed Sparrows, other sparrows |
| Screech Owl | Ruffed Grouse, pigeons, quail, Eastern Phoebe, Horned Lark, Blue Jay, starling, blackbirds, American Goldfinch, juncos, sparrows |
| Snowy Owl | Grebes, ducks, coots, sandpipers, crows |

Hawks that consume birds include the red-shouldered hawk, the red-tailed hawk, the rough-legged hawk, the broad-winged hawk, the American kestrel, the sharp-shinned hawk, the Cooper's hawk, and the marsh hawk.

Figure 3:
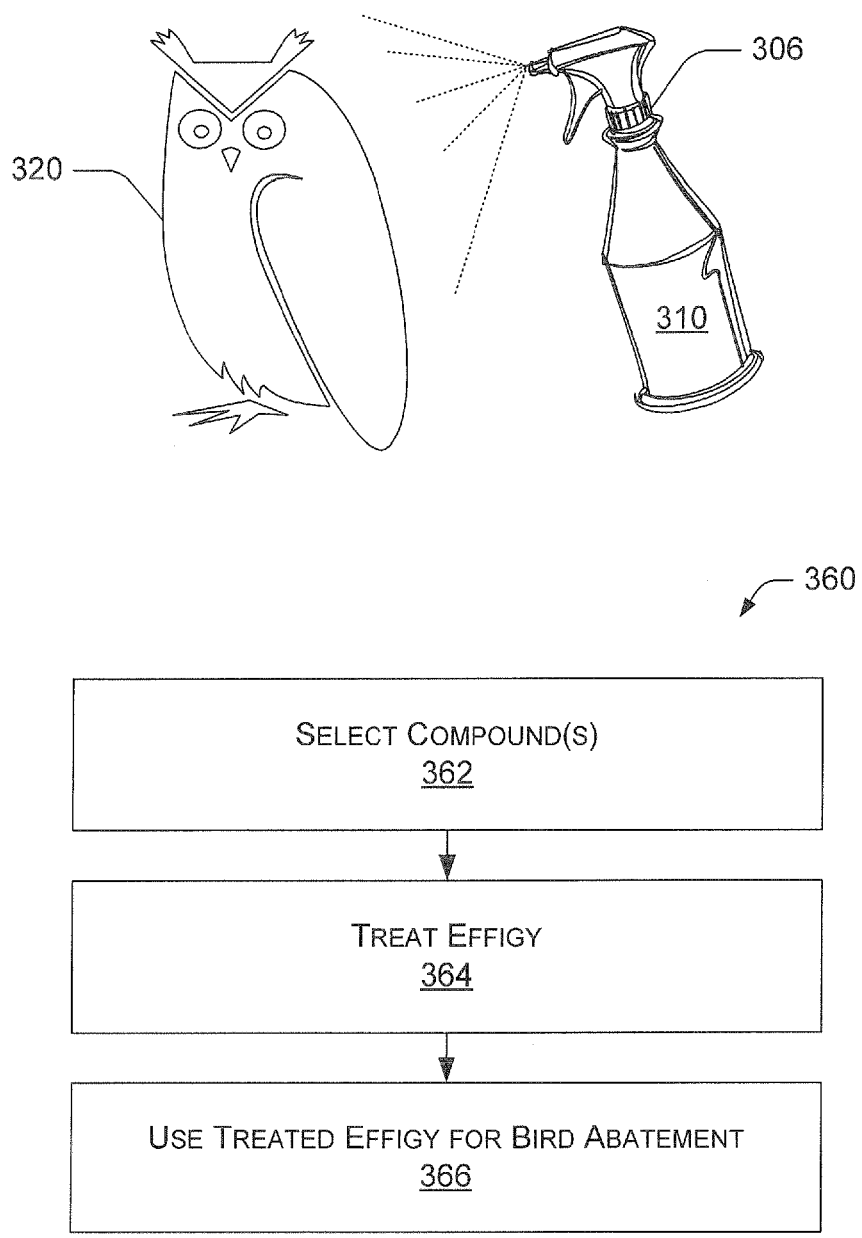
FIG. 3 is a diagram of an exemplary device and method for treating an effigy.

FIG. 3 shows an exemplary method 300 for treating an effigy. According to the method 300, an effigy 320 is treated with a compound 310 that irritates birds. In the example of FIG. 3, a compound 310 is sprayed onto the effigy 320 using a spray mechanism such as a spray bottle 306. A specific method 360 includes selecting one or more compounds that irritate birds (e.g., promote avoidance behavior) 362, treating an effigy with the selected one or more compounds 364 and then using the treated effigy for bird abatement 366. If desired, the method 360 may be repeated to "refresh" the effigy. For example, such treatment may occur on a monthly basis.

Figure 4:
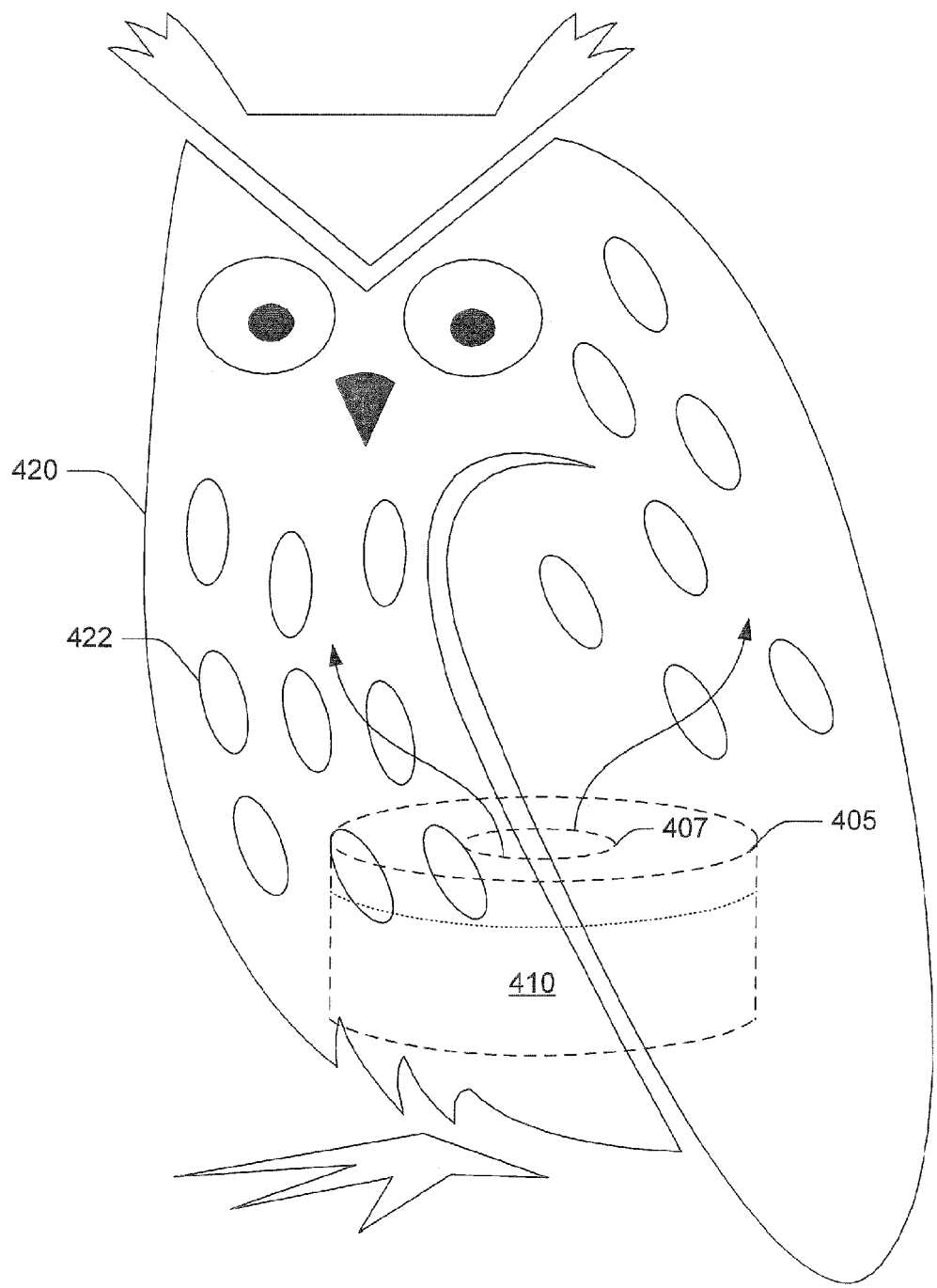
FIG. 4 is an illustration of an exemplary effigy with a container for a compound that affects bird behavior.

FIG. 4 shows an exemplary device 400 for affecting the behavior of birds. The device 400 includes an effigy 420 that includes a plurality of orifices 422. In the example of FIG. 4, the effigy 420 houses a container 405 that includes an opening 407 (e.g., wick, aperture, etc.) that allows a compound 410 to exit the container 405 and traverse the orifices 422. Such a device may also be treated according to the method 300 of FIG. 3.

In some instances, a compound may have light sensitivity and an effigy may act to protect or shade a reservoir containing the compound from light. While the device 400 shows the container 405 as having a cylindrical shape, other shapes are possible. Further, a sponge, foam or other material may be used to contain a compound. For example, an exemplary effigy can include a foam core that can be at least partially filled with a compound and released in an environment via diffusion, convection, etc., to repel birds. In such an example, the foam core may be refilled periodically. While foam is mentioned, other porous substrates may be used (e.g., ceramics, plastics, wood, etc.).

An exemplary effigy can include a container for the purpose of containing a repellent substance. The container may include a porous substrate or other substrate to wick repellent from the container via capillary action and transport the repellent to a surface where diffusion may occur to the surrounding environment.

An effigy is optionally constructed from a porous, absorbent and/or amorphous material capable of acting as a time release mechanism for a repellent. In general, passive techniques for time release may include use of absorbent material, porous material, gel, wax or other amorphous material used to delay dissipation. One trial included use of papier mâché as an absorbent material or carrier (Celuclay II, Activa Products, Inc., Marshall, Tex.). Another trial included use of blotter paper cut in the form of an owl where the blotter paper acted as an absorbent for lengthening the time that repellency was maintained. Such techniques may be used in conjunction with an effigy and optionally be integral with an effigy (e.g., an effigy formed from a porous material). While various examples discuss birds, an effigy may be configured to act more generally to repel animals where the effigy alone has some avoidance characteristics with respect to one or more target animals and where the effigy includes a mechanism to introduce a repellent for at least one of those target animals.

Various trials used owl effigies for bird abatement. In one example, a repellent (MA) was poured over sawdust. After the sawdust absorbed the repellent, a hollow owl effigy was filled with the sawdust. This example is discussed in more detail with respect to FIGS. 8A-D. In an alternative process, the hollow effigy could be filled with the sawdust and then treated with the repellent. In another example, repellent was applied to absorbent paper having a thickness of about 0.25 inch (0.6 cm). The absorbent paper was positioned between two cardboard owl cutouts, which had owl eyes and other owl features. Repellent was able to diffuse from the absorbent paper outwardly via the sides of the assembled effigy. This assembled and treated effigy could be hung from a rafter or a line. While this example used absorbent paper, materials such as paraffin, natural or synthetic sponge, etc., can be used.

As mentioned, a snake effigy may be used for bird abatement. A snake effigy having a core filled with porous, spongy beads was treated with MA. In this example, MA was injected into the core of the snake effigy where the beads acted as absorbent to slow release of MA from the snake effigy. This example is discussed in more detail with respect to FIGS. 9A and 9C. In another example, a ribbed snake effigy having open belly side compartments was treated with MA by filling the compartments with a mixture of paraffin and MA. This example is discussed in more detail with respect to FIGS. 9A and 9B.

Figure 5:
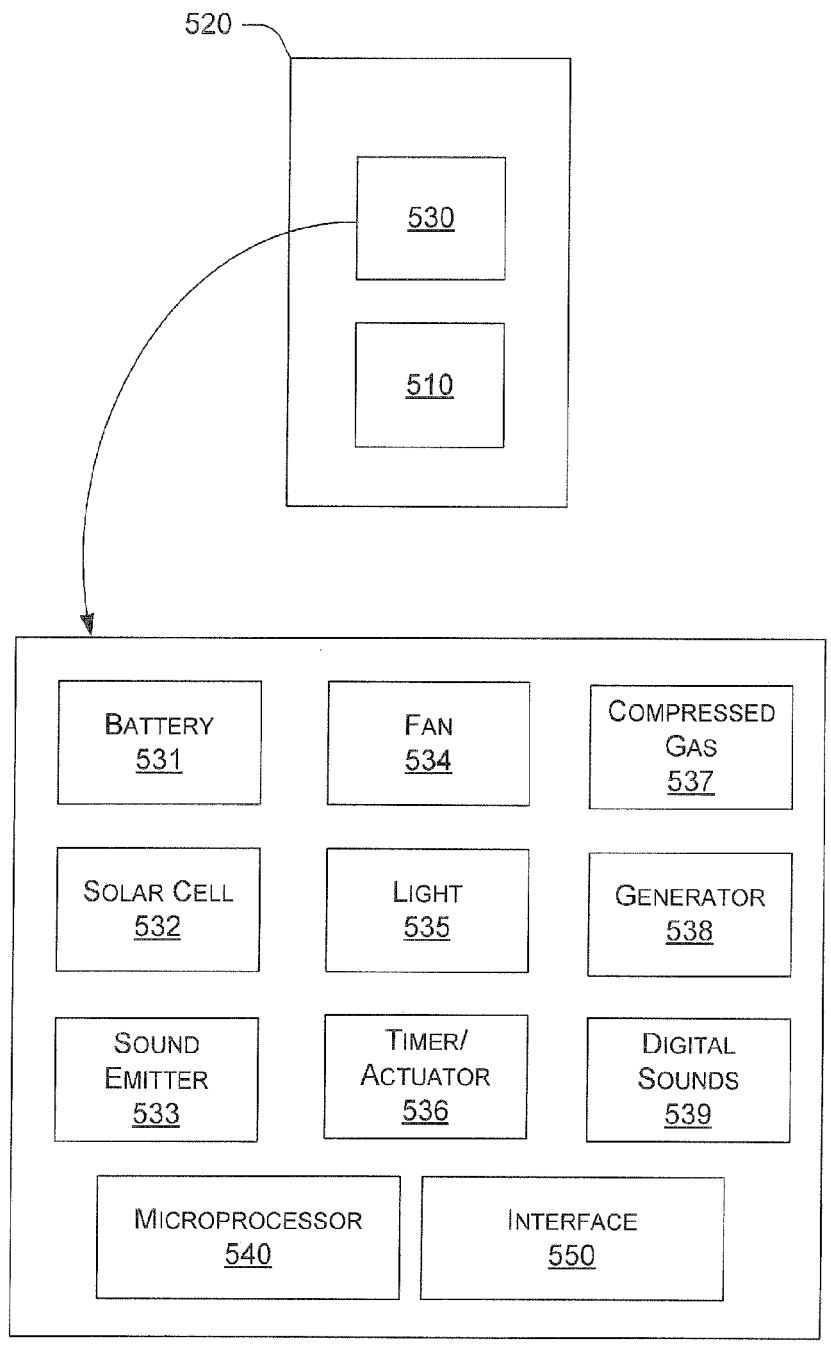
FIG. 5 is a block diagram of an exemplary effigy that includes electronic circuitry as well as a compound that affects bird behavior.

FIG. 5 shows an exemplary device 500 that includes electronic circuitry 530 in addition to a compound to repel birds 510. The circuitry 530 may include or operate in conjunction with one or more of the following: a battery 531, a solar cell 532 (for energy or light control), a sound emitter 533, a fan 534, a light 535 (to signal a condition and/or to repel birds), a timer/actuator 536 (e.g., to cause an action to occur), a container of compressed gas 537 (e.g., to inflate or move a component of an effigy, to produce a sound, to propel material, to transport a compound by convection, etc.), a generator 538 (e.g., to generate energy from a hand crank or wind), digital sounds 539 (e.g., predator sounds, distress sounds, etc.), a microprocessor 540 and an interface 550. The interface 550 may be a user hand switchable/selectable interface, a wired interface or a wireless interface (e.g., radio, infrared, etc.).

Figure 6:
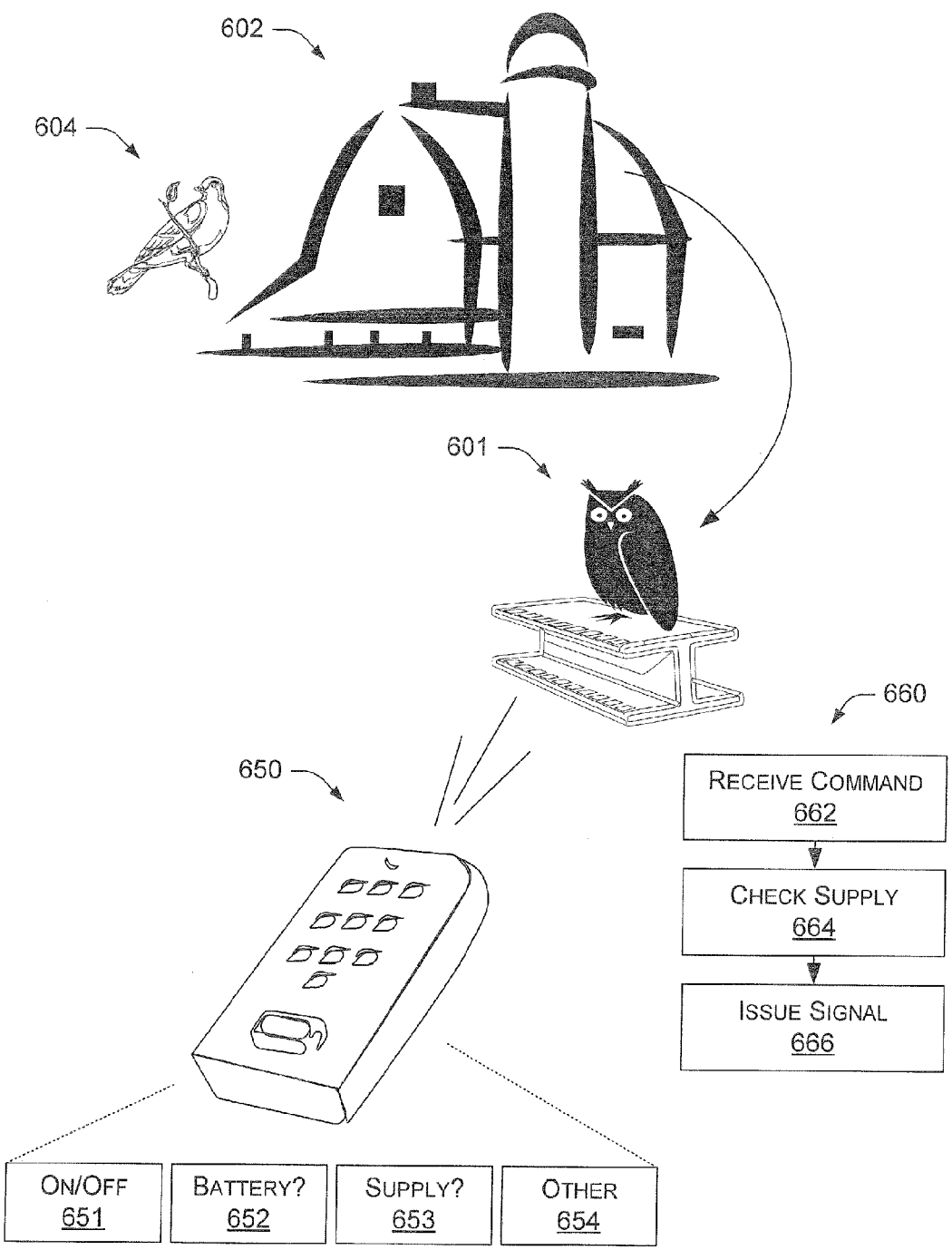
FIG. 6 is a schematic of a method for issuing one or more commands to an exemplary effigy where the effigy includes electronic circuitry for responding to a command.

FIG. 6 shows an exemplary scheme 600 that includes a structure 602 such as a shed or barn. Neighboring the structure 602 are nuisance birds 604 such as pigeons. The scheme 600 includes an exemplary effigy 601 positioned in a manner visible to a nuisance bird 604 from outside the structure 602 and/or from within the structure 602. The effigy 601 may be a treated effigy as shown in FIG. 3, an effigy containing a supply of an irritant compound as shown in FIG. 4, an effigy that includes electronic circuitry as shown in FIG. 5 or an effigy that includes a combination of one or more features of these effigies.

Where the effigy 601 includes electronic circuitry to respond to a signal emitted by a command device 650, the effigy 601 may operate according to a method 660. The method 660 includes receiving a transmitted command 662, checking a supply 664 (e.g., irritant compound, power supply, etc.), and issuing a signal 666 where the signal pertains to the supply. For example, the effigy 601 may issue an auditory signal, a visual signal (light or movement) or other type of signal (e.g., radio, infrared, etc.). A signal may indicate that supply of an irritant compound is sufficient or depleted or that power is sufficient or nearly depleted (e.g., akin to a smoke detector battery depletion signal).

The command device 650 may issue any of a variety of commands (e.g., a remote controller for one or more functions as described with respect to FIG. 5). FIG. 6 shows some commands: on/off 651, battery check 652, supply check 653, other 654. As the effigy 601 may be placed high in a structure such as a barn, the command device 650 may allow for remote assessment and/or control and thereby alleviate the need for frequent physical access to the effigy.

An effigy optionally includes one or more eyelets or similar mechanism that provide for attachment of a line or pole to facilitate placement and positioning of an effigy. For example, an effigy may work in cooperation with a pulley system. With respect to the treatment method 300 of FIG. 3, an effigy may be hoisted in a shed or other structure via a pulley system and then periodically lowered, retreated and repositioned.

Figure 7:
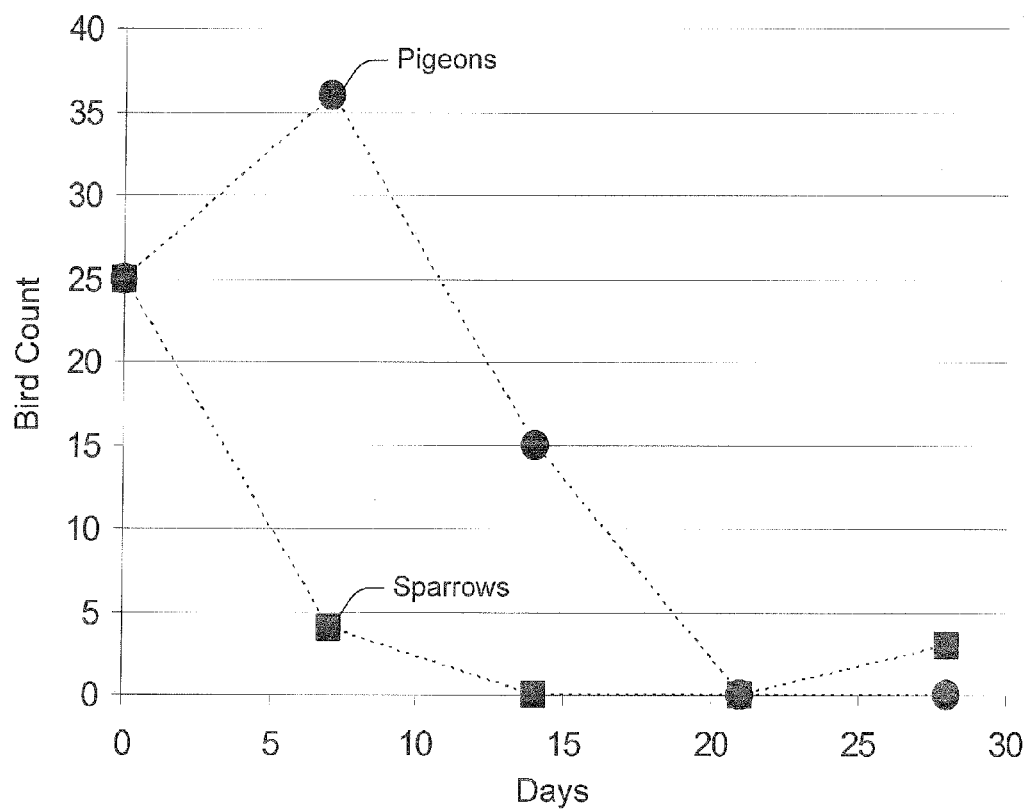
FIG. 7 is a plot of a trial using an exemplary effigy manufactured according to the method of FIG. 3.

FIG. 7 shows a plot of data collected from a trial of an exemplary treated effigy prepared according to the method 300 of FIG. 3. In this trial an owl effigy was treated with a composition that included MA at about 26.4% (73.6% inert). The trial occurred in an open air equipment storage barn in Sacramento, Calif. More specifically, the structure was classified as a wood structure roof with pole barn and a square footage of about 5,000 square feet (dimensions 100 feet by 50 feet). The structure was frequently occupied by pigeons and sparrows. The structure was selected as it experienced economically significant levels of roosting and/or nesting birds. The goal was to repel birds that created damage to parked or stored maintenance equipment, trucks and tractors. The trial occurred during the month of January.

The treated effigy was hung with bailing wire from the roof onto a rafter in the center of barn. The plot 700 shows the approximate avian population before and during the trial. Observations in accord with the plot 700 are provided below.

Pre Installation Numbers and Species:
30 to 50 mixed of Pigeons and Sparrows (non nesting)
Day of Installation:
50 to 60 mixed of Pigeons and Sparrows
7 Days after Installation:
30 to 40 (90% Pigeons and 10% Sparrows)
14 Days after Installation:
Pigeons, and no Sparrows
21 Days after Installation:
0 Pigeons, and 0 Sparrows
28 Days after Installation:
0 Pigeons, and 3 Sparrows
End of Evaluation Trial observations indicate that the use of an exemplary effigy (MA treated owl) has an efficacious impact at controlling birds in an open air, roofed area. The full benefit of reduced populations of roosting birds occurred between about 14 and about 21 days. Re-treatment of the effigy with MA can extend the benefit, if needed or desired.

Figure 8A:
FIGS. 8A-D are photographs of an exemplary process and an exemplary device for repelling birds.
Figure 8B:
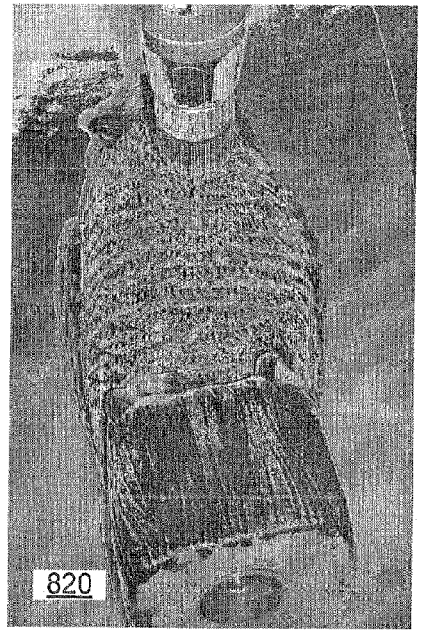
Figure 8C:
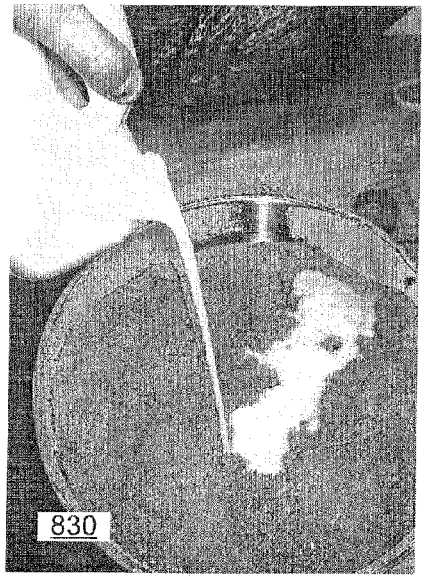
Figure 8D:
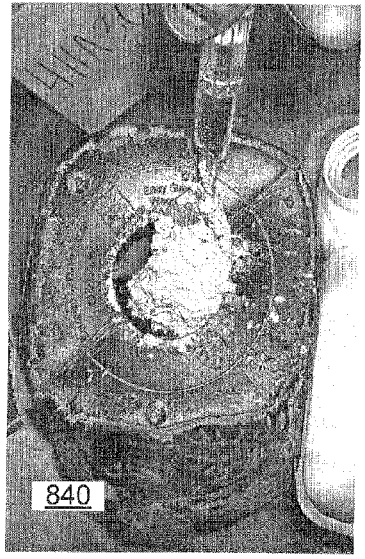

FIGS. 8A-D show an exemplary process and an exemplary device for repelling birds. FIG. 8A shows a plastic owl, provided for filling with a repellent compound 810. FIG. 8B shows a drilling process 820 for drilling holes in the plastic owl. FIG. 8C shows a mixing process 830 for mixing a repellent material (in this example, the repellent material includes MA) with a carrier, which in this example was sawdust, to create a fill material. FIG. 8D shows a filling process 840 for filling the plastic owl with the fill material. In this example, the plastic owl had a capped opening on its base. After filling the plastic owl with the fill material, the base opening is capped with a cap. The repellent device is then ready to use. In this example, the carrier caries the repellent material and retards the release through the holes, which compared to an equivalent open container of the repellent material, prolongs the ability of the device to repel birds via chemical means. This approach can also prolong the duration of the combined fright/irritant effect, which can help promote association of fright with irritant and irritant with fright.

Figure 9A:
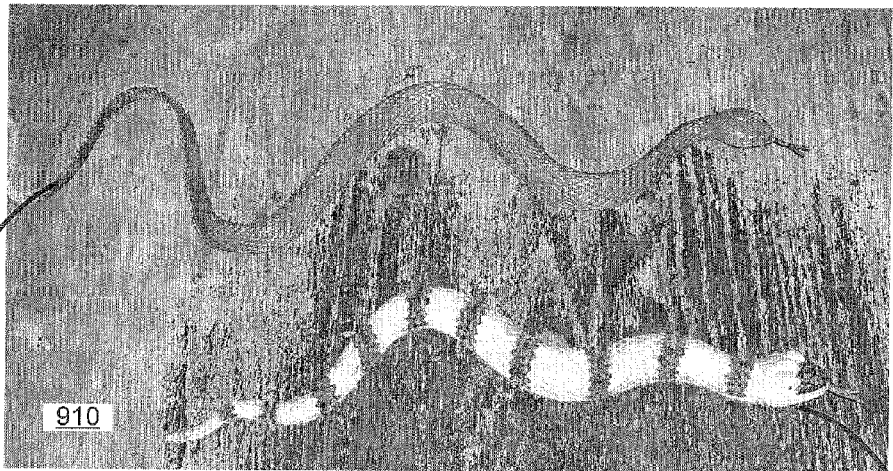
FIGS. 9A-C are photographs of two exemplary processes and two exemplary devices for repelling birds.
Figure 9B:
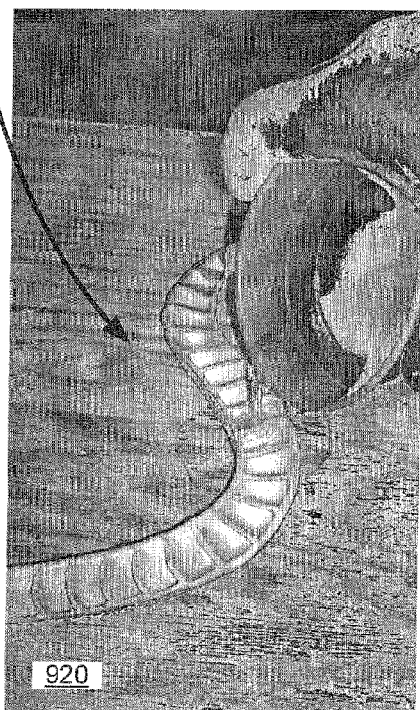
Figure 9C:
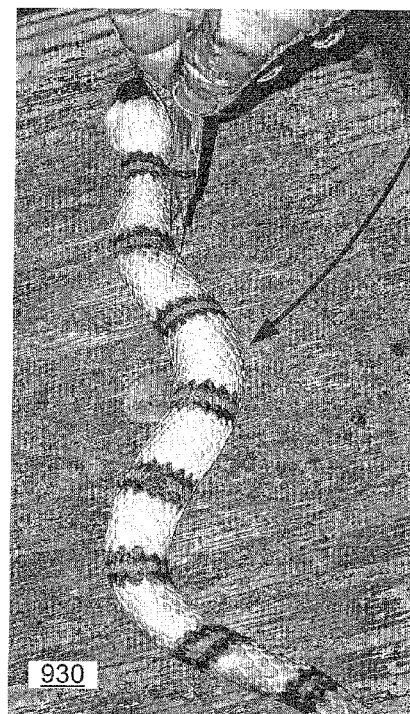

FIGS. 9A-C show two exemplary processes and two exemplary devices. FIG. 9A shows two snakes, provided for filling with a repellent compound 910. One snake may be a predator of a certain avian species and the other snake may be a predator of a different avian species. Snakes or other predators may be provided with different coloring, shape, size, configuration, etc. For example, where plumage of a predator animal varies with season, an effigy with winter plumage and an effigy with summer plumage may be used simultaneously or in season. A snake may be serpentine in configuration, coiled, etc. A snake may be positioned on the ground, in a tree, on a fence, etc.

FIG. 9B shows a filling process 920 where a repellent material (including paraffin and MA) is poured into open compartments on the under side of the upper snake of FIG. 9A. The repellent material may solidify to some extent after filling (e.g., wax, gel, etc.). Once filled, the snake can be placed in, for example, a vineyard to repel birds from wine grapes. In such an example, the wine grapes are not "treated" with the repellent material; hence, environmental and/or organic standards may be met for the wine grapes while still repelling birds.

FIG. 9C shows a filling process 930 where a repellent material is injected into the interior portion of the lower snake of FIG. 9B. In this example, the snake is commercially available with a filler material (e.g., beads) and then the repellent material (including MA) is added via injection (e.g., via a syringe or other injector). Filler material and/or material of construction of exterior portion of the snake may be chosen to control dissipation of a repellent compound residing in the interior portion. For example, porosity of the exterior portion may be chosen to adjust diffusion of repellent from the interior portion.

As mentioned, various devices, methods, systems, etc., may be used for abating birds from crops used in organic products or, more generally, sold as organic produce. With respect to organic labeling and certification, being able to put the word "organic" on a food product is a valuable marketing advantage in today's consumer market. Certification is intended to protect consumers from misuse of the term, and make buying organics easy. In the US, federal organic legislation defines three levels of organics (see, e.g., 7 CFR Part 205, "National Organic Program", USDA). Products made entirely with certified organic ingredients and methods can be labeled "100% organic". Products with 95% organic ingredients can use the word "organic". Both may also display the USDA organic seal. A third category, containing a minimum of 70% organic ingredients, can be labeled "made with organic ingredients". In addition, products may also display the logo of the certification body that approved them. Products made with less than 70% organic ingredients can not advertise this information to consumers and can only mention this fact in the product's ingredient statement. Similar percentages and labels apply in the European Union.

As mentioned, various devices, methods, systems, etc., may be used for abating birds from crops in a manner that does not alter the flavor of the crop. For example, the repellent MA is not recommended for treating wine varietals as it imparts a "foxy" character. Foxy refers to the odors and tastes of wines made from many of the American species of grape (i.e., *vitis labrusca*) and is caused by in part by MA. A foxy wine smells and tastes like Concord grape juice as Concord grapes produce MA. As described herein, an effigy that includes a repellent may be positioned in a vineyard to abate birds. As the repellent is not applied to the vines or grapes, risk of a foxy characteristic is minimized and yields may be increased as losses due to birds are reduced.

With respect to crops, various effigy/repellent devices may be used for grapes, strawberries, sunflowers, etc. However, bird losses do not only stem from mere consumption of crops. For example, birds cause significant losses in vineyards, not only from the fruit they eat but also from the spoilage they initiate. Once a berry is pecked or damaged, the juice is released and secondary spoilage organisms such as *acetobacter, penicillium, botrytis* and others will move in and cause bunch and sour rots. If grapes are mechanically harvested, the rotten grapes taint the flavor of the wine; it is possible, but difficult, to sort the grapes, either in the field or at the winery. A common approach to bird control in vineyards is netting. Netting is expensive both to purchase and to use (about $700 to $1000 per acre depending on spacing). Thus, various exemplary techniques described herein offer viable and economical alternatives to conventional bird abatement techniques.

The invention claimed is:

1. An assembly comprising:
   a hollow owl effigy that comprises holes;
   methyl anthranilate; and
   a carrier to carry the methyl anthranilate within the hollow owl effigy and to retard release of the methyl anthranilate through the holes of the hollow owl effigy.

2. The assembly of claim 1 wherein the hollow owl effigy comprises plastic.

3. The assembly of claim 1 wherein the carrier comprises sawdust.

4. The assembly of claim 1 wherein the carrier comprises paper.

5. The assembly of claim 1 wherein the carrier comprises foam.

6. The assembly of claim 1 wherein the carrier comprises sponge.

7. The assembly of claim 1 wherein the carrier comprises wax.

8. The assembly of claim 1 wherein the carrier comprises gel.

9. The assembly of claim 1 comprising a cap to cap an opening and wherein the hollow owl effigy comprises the opening.

10. The assembly of claim 1 wherein the hollow owl effigy comprises an attachment mechanism to attach the hollow owl effigy to a line or a pole.

11. The assembly of claim 10 wherein the attachment mechanism comprises one or more eyelets.

12. The assembly of claim 1 further comprising a pulley system for positioning the hollow owl effigy.

13. The assembly of claim 12 wherein the assembly comprises, with respect to a structure, a lowered state of the hollow owl effigy for retreatment of the carrier with additional methyl anthranilate.

14. The assembly of claim 1 further comprising additional methyl anthranilate to retreat the carrier after release of at least some of the methyl anthranilate.

15. A method comprising:
   providing a hollow owl effigy that comprises holes and an opening;
   mixing methyl anthranilate with a carrier;
   filling the hollow owl effigy with the carrier and the methyl anthranilate; and
   capping the opening with a cap wherein the carrier comprises an absorbent material from which the methyl anthranilate can diffuse.

16. The method of claim 15 wherein the carrier comprises saw dust or paper.

17. The method of claim 15 further comprising hoisting the filled, capped hollow owl effigy within a structure.

\* \* \* \* \*